US007566785B2

(12) United States Patent
Linsell et al.

(10) Patent No.: US 7,566,785 B2
(45) Date of Patent: Jul. 28, 2009

(54) AMIDINE SUBSTITUTED ARYL ANILINE COMPOUNDS

(75) Inventors: Martin S. Linsell, San Mateo, CA (US); John R. Jacobsen, San Mateo, CA (US); Ningning Xu, Lawrenceville, NJ (US)

(73) Assignee: Theravance, Inc., South San Francisco, CA (US)

( * ) Notice: Subject to any disclaimer, the term of this patent is extended or adjusted under 35 U.S.C. 154(b) by 597 days.

(21) Appl. No.: 11/222,413

(22) Filed: Sep. 8, 2005

(65) Prior Publication Data

US 2006/0058530 A1   Mar. 16, 2006

Related U.S. Application Data

(60) Provisional application No. 60/609,189, filed on Sep. 10, 2004.

(51) Int. Cl.
*C07D 215/00* (2006.01)
*A61K 31/497* (2006.01)
(52) U.S. Cl. .................................. 546/157; 514/253.07
(58) Field of Classification Search ................. 546/312; 564/123
See application file for complete search history.

(56) References Cited

U.S. PATENT DOCUMENTS

| 3,875,233 | A | 4/1975 | Bastian et al. |
|---|---|---|---|
| 4,021,485 | A | 5/1977 | Schromm et al. |
| 4,894,219 | A | 1/1990 | Baker et al. |
| 4,992,474 | A | 2/1991 | Skidmore et al. |
| 5,223,614 | A | 6/1993 | Schromm et al. |
| 5,434,304 | A | 7/1995 | Trofast et al. |
| 5,750,701 | A | 5/1998 | Beeley et al. |
| 6,265,581 | B1 | 7/2001 | Bell et al. |
| 6,268,533 | B1 | 7/2001 | Gao et al. |
| 6,297,382 | B1 * | 10/2001 | Scott ........................ 546/276.4 |
| 6,537,983 | B1 | 3/2003 | Biggadike et al. |
| 6,541,669 | B1 | 4/2003 | Moran et al. |
| 6,576,793 | B1 | 6/2003 | Moran et al. |
| 6,653,323 | B2 | 11/2003 | Moran et al. |
| 6,670,376 | B1 | 12/2003 | Moran et al. |
| 6,747,043 | B2 | 6/2004 | Moran et al. |
| 6,759,398 | B2 | 7/2004 | Biggadike |
| 6,825,220 | B2 | 11/2004 | Jesudason et al. |
| 6,878,721 | B1 | 4/2005 | Cuenoud et al. |
| 6,919,482 | B2 | 7/2005 | Moran et al. |
| 6,949,568 | B2 | 9/2005 | Moran et al. |
| 2002/0019378 | A1 | 2/2002 | Angell et al. |
| 2002/0022625 | A1 | 2/2002 | Walland et al. |
| 2002/0143034 | A1 | 10/2002 | Taniguchi et al. |
| 2003/0229058 | A1 | 12/2003 | Moran et al. |
| 2004/0006143 | A1 | 1/2004 | Hattori et al. |
| 2004/0063755 | A1 | 4/2004 | Moran et al. |
| 2004/0157830 | A1 | 8/2004 | Biggadike et al. |
| 2004/0180876 | A1 | 9/2004 | Biggadike et al. |
| 2004/0224982 | A1 | 11/2004 | Axt et al. |
| 2004/0242890 | A1 | 12/2004 | Coe et al. |
| 2004/0248985 | A1 | 12/2004 | Stergiades et al. |
| 2005/0075271 | A1 | 4/2005 | Linsell et al. |
| 2005/0075394 | A1 | 4/2005 | Box et al. |
| 2005/0113411 | A1 | 5/2005 | Linsell et al. |
| 2005/0159448 | A1 | 7/2005 | McKinnell et al. |
| 2005/0209275 | A1 | 9/2005 | Moran et al. |
| 2005/0209338 | A1 | 9/2005 | Blake et al. |
| 2005/0272769 | A1 | 12/2005 | Linsell |
| 2006/0019991 | A1 | 1/2006 | McKinnell et al. |
| 2007/0155990 | A1 | 7/2007 | Stergiades et al. |
| 2007/0225329 | A1 | 9/2007 | Moran et al. |

FOREIGN PATENT DOCUMENTS

| BE | 849 794 | 4/1977 |
|---|---|---|
| CH | 550 768 | 2/1972 |
| EP | 0 233 686 A2 | 8/1987 |
| EP | 0147 719 B1 | 7/1989 |
| EP | 0 196 849 A2 | 10/1996 |
| GB | 1040724 | 9/1966 |
| GB | 1 463 219 | 2/1977 |
| JP | 52-83379 | 7/1977 |
| JP | 52-83619 | 7/1977 |
| WO | WO 01/07026 A2 | 2/2001 |
| WO | WO 02/00622 A2 | 1/2002 |
| WO | WO 03/091204 A1 | 11/2003 |
| WO | WO 2004/016578 A2 | 2/2004 |

OTHER PUBLICATIONS

U.S. Appl. No. 11/185,295, filed Jul. 20, 2005, McKinnell et al.
Bompart et al., "Synthesis of new β-blocking analogs of bevantolol", Annales Pharmaceutiques Francaises, Volume Date 1984, 42(6), pp. 537-545 (1985) (In French with English abstract).
Bompart et al., "Synthesis of new β-blocker analogs of bevantolol or alprenolol", Annales Pharmaceutiques Francaises, Volume Date 1987, 45(5), pp. 379-387 (1988) (In French with English abstract).
Deyrup et al., "Structure-affinity profile of 8-hydroxycarbostyril-based agonists that dissociate slowly from the Beta2-adrenoceptor", Naunyn-Schmiedeberg's Arch Pharmacol (1999) 359:168-177.
Isogaya et al., "Binding Pockets of the $\beta_1$- and $\beta_2$-Adrenergic Receptors for Subtype-Selective Agonists"), Molecular Pharmacology, vol. 56, pp. 875-885 (1999).
Milecki et al., "Carbostyril Derivatives Having Potent β-Adrenergic Agonist Properties", J. Med. Chem., (1987), 30, 1563-1566.
Yokoi et al., "The Development of a Radioimmunoassay for Formoterol", Life Sciences, (1983) vol. 33, No. 17, pp. 1665-1672.
Yoshizaki et al., "Sympathomimetic Amines Having a Carbostyril Nucleus", J. Med. Chem., (1976), vol. 19, No. 9, pp. 1138-1142.

* cited by examiner

*Primary Examiner*—Rita J Desai
*Assistant Examiner*—John Mabry
(74) *Attorney, Agent, or Firm*—Jeffrey A. Hagenah; Roberta P. Saxon

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

9 Claims, No Drawings

AMIDINE SUBSTITUTED ARYL ANILINE COMPOUNDS

CROSS-REFERENCE TO RELATED APPLICATIONS

This application claims the benefit of U.S. Provisional Application No. 60/609,189, filed on Sep. 10, 2004, the disclosure of which is incorporated herein by reference in its entirety.

FIELD OF THE INVENTION

The present invention is directed to amidine substituted aryl aniline compounds, pharmaceutical compositions comprising such compounds, methods for using such compounds, and processes for preparing such compounds.

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable duration of action, potency, selectivity, and/or onset.

Thus, there is a need for novel $\beta_2$ adrenergic receptor agonists having improved properties, such as improved duration of action, potency, selectivity, and/or onset.

SUMMARY OF THE INVENTION

The present invention provides amidine substituted aryl aniline compounds of the Formula I:

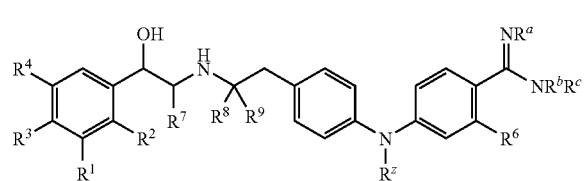

I or a pharmaceutically acceptable salt or solvate or stereoisomer thereof;

wherein
each of $R^1$, $R^2$, $R^3$, and $R^4$ is independently selected from hydrogen, hydroxy, $C_{1-6}$ alkoxy, —$NR^eR^f$, halo, $C_{1-6}$ hydroxyalkyl and —NHCHO, wherein each of $R^e$ and $R^f$ is independently hydrogen or $C_{1-6}$ alkyl, or $R^1$ and $R^2$ taken together are selected from —NHC(=O)CH=CH—, —CH=CHC(=O)NH—, —NHC(=O)S—, and —SC(=O)NH—;
$R^a$ is hydrogen, $C_{1-6}$ alkyl, or hydroxy;
each of $R^b$ and $R^c$ is independently hydrogen, $C_{1-6}$ alkyl, or $C_{3-10}$ cycloalkyl, or $R^b$ and $R^c$ together with the nitrogen atom to which they are attached form a heterocyclyl ring having from 5 to 7 ring atoms and containing 1 to 3 heteroatoms selected from nitrogen, oxygen and sulfur, or $R^a$ and $R^b$ taken together form $C_{2-4}$ alkylene;
$R^6$ is hydrogen, hydroxy, halo, $C_{1-4}$ alkoxy, $C_{1-4}$ alkyl, or $C_{1-4}$ haloalkyl; and
each of $R^7$, $R^8$, $R^9$, and $R^z$ is independently hydrogen or $C_{1-6}$ alkyl.

Compounds of the present invention possess a variety of physiological properties. Some of the physiological properties exhibited by compounds of the present invention include $\beta_2$ adrenergic receptor agonist activity. Compounds of the present invention are potent and selective $\beta_2$ adrenergic receptor agonists.

The present invention also provides a pharmaceutical composition comprising a therapeutically effective amount of a compound of Formula I and a pharmaceutically acceptable excipient.

In addition, the present invention provides a combination comprising a compound of Formula I and one or more other therapeutic agents and a pharmaceutical composition comprising a combination of the invention and a pharmaceutically acceptable excipient.

The present invention also provides a method of treating a mammal having a disease or condition associated with $\beta_2$ adrenergic receptor activity (e.g., a pulmonary disease, such as asthma or chronic obstructive pulmonary disease, pre-term labor, a neurological disorder, a cardiac disorder, or inflammation). The method typically comprises administering to the mammal, a therapeutically effective amount of a compound of Formula I or any of the pharmaceutical compositions comprising a compound of Formula I as disclosed herein. In particular, the invention provides a method of treating asthma or chronic obstructive pulmonary disease in a mammal, the method comprising administering to the mammal, a therapeutically effective amount of a compound of the invention.

The invention further provides a method of treatment comprising administering a therapeutically effective amount of a combination of a compound of the invention and one or more other therapeutic agents.

The present invention also provides a method for treating a $\beta_2$ adrenergic receptor activity mediated disorder comprising administering to a patient a therapeutically effective amount of a compound of Formula I.

In addition, the present invention provides a process for producing an amidine substituted aryl aniline compound of Formula IF:

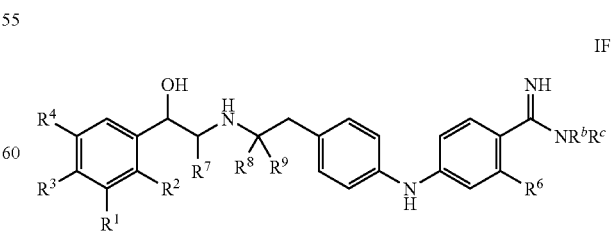

IF wherein $R^1$, $R^2$, $R^3$, $R^4$, $R^6$, $R^7$, $R^8$, $R^9$, $R^b$, and $R^c$ are defined as in Formula I, the process comprising:

(a) reacting an aryl compound of Formula II:

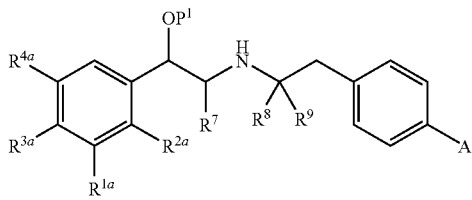

with a cyanophenyl compound of Formula III:

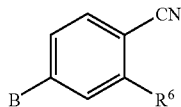

wherein

P$^1$ is a hydroxy-protecting group, each of R$^{1a}$, R$^{2a}$, R$^{3a}$, and R$^{4a}$ is defined to be the same as R$^1$, R$^2$, R$^3$, and R$^4$, respectively, in Formula I, or, when any of R$^1$, R$^2$, R$^3$, and R$^4$ comprises a hydroxy or an amino group, the corresponding R$^{1a}$, R$^{2a}$, R$^{3a}$, and R$^{4a}$ group optionally comprises a protected hydroxy or a protected amino group, and one of A and B is halo and the other of A and B is —NH$_2$, in the presence of a coupling catalyst under conditions sufficient to produce a cyano-substituted aryl aniline compound of Formula IV:

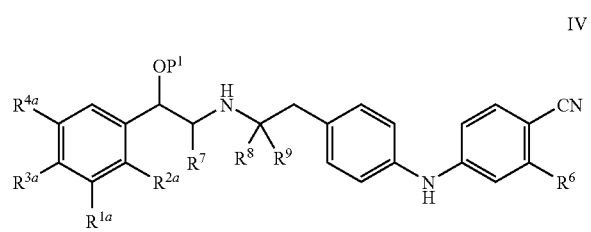

(b) reacting the cyano-substituted aryl aniline compound of Formula IV in the presence of an acid and under conditions sufficient to produce an iminoester compound of Formula VI:

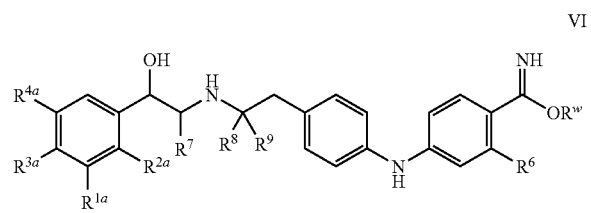

wherein R$^w$ is C$_{1-6}$ alkyl;

(c) reacting the iminoester compound of Formula VI with an amine compound of the formula HNR$^b$R$^c$ under conditions sufficient to produce a compound of Formula IG;

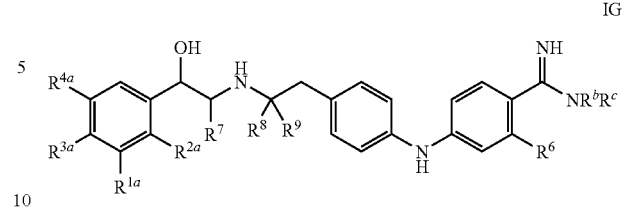

and (d) optionally removing any hydroxy- or amino-protecting group that may be present in any of R$^{1a}$, R$^{2a}$, R$^{3a}$, and R$^{4a}$ under conditions sufficient to produce said amidine substituted aryl aniline compound of Formula IF.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new β$_2$ adrenergic receptor agonists.

The invention also provides other synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with β$_2$ adrenergic receptor activity, e.g., a pulmonary disease, such as asthma or chronic obstructive pulmonary disease, pre-term labor, a neurological disorder, a cardiac disorder, or inflammation, in a mammal.

DETAILED DESCRIPTION OF THE INVENTION

Definitions

The term "alkyl" means a monovalent saturated hydrocarbon group which may be linear or branched. Unless otherwise defined, linear alkyl groups typically contain from 1 to 10 carbon atoms and branched alkyl groups typically contain 3 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkoxy" means a monovalent moiety of the formula —O-alkyl, where alkyl is as defined herein. Representative alkoxy groups include, by way of example, methoxy, ethoxy, propoxy, butoxy, and the like.

The term "alkylene" means a divalent saturated hydrocarbon group which may be linear or branched. Unless otherwise defined, such linear alkylene groups typically contain from 1 to 10 carbon atoms and branched alkylene groups typically contain from 3 to 10 carbon atoms. Representative alkylene groups include, by way of example, methylene, ethylene, n-propylene, n-butylene, 1-methylethylene, 1,1-dimethylethylene, and the like.

The term "cycloalkyl" means a monovalent saturated or partially unsaturated cyclic non-aromatic hydrocarbon group, which may be monocyclic or multicyclic (i.e., fused or bridged). Unless otherwise defined, such cycloalkyl groups typically contain from 3 to 10 total ring atoms. Representative cycloalkyl groups include, cyclopropyl, cyclobutyl, cyclopentyl, cyclohexyl, and the like.

The term "heterocyclyl" or "heterocyclic ring" means a monovalent saturated or partially unsaturated cyclic non-aromatic group, which may be monocyclic or multicyclic (i.e., fused or bridged), and which contains at least one heteroatom (typically 1 to 3 heteroatoms) selected from nitrogen, oxygen, and sulfur. Unless otherwise defined, such heterocyclyl groups typically contain from 5 to 10 total ring atoms. Representative heterocyclyl groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl, and the like.

The term "halo" means a fluoro, chloro, bromo or iodo.

The term "hydroxyalkyl" means an alkyl group, as defined herein, which is substituted with one or more, typically one, hydroxy group(s), provided that if two or more hydroxy groups are present, they are not both on the same carbon atom. Unless otherwise defined, such hydroxyalkyl groups typically contain from 1 to 10 carbon atoms. Exemplary hydroxyalkyl groups include, hydroxymethyl (—$CH_2OH$), 2-hydroxyethyl (—$CH_2CH_2OH$), 1-hydroxyethyl (—$CH(OH)CH_3$), and the like.

The term "haloalkyl" means an alkyl group, as defined herein, which is substituted with one or more halo substituent(s). Unless otherwise defined, such haloalkyl groups typically contain from 1 to 10 carbon atoms. Exemplary haloalkyl groups include, difluoromethyl (—$CHF_2$), trifluoromethyl (—$CF_3$), 2,2,2-trifluoroethyl (—$CH_2CF_3$), and the like.

The term "therapeutically effective amount" means an amount sufficient to effect treatment when administered to a patient in need of treatment.

The term "treatment" as used herein means the treatment of a disease or medical condition in a patient, such as a mammal (particularly a human) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The phrase "disease or condition associated with $\beta_2$ adrenergic receptor activity" encompasses all medical conditions alleviated by treatment with a $\beta_2$ adrenergic receptor agonist and includes all disease states and/or conditions that are acknowledged now, or that are found in the future, to be associated with $\beta_2$ adrenergic receptor activity. Such disease states include, but are not limited to, pulmonary diseases, such as asthma and chronic obstructive pulmonary disease (including chronic bronchitis and emphysema), as well as neurological disorders and cardiac disorders. (See, for example, Emilien et al. "Current therapeutic uses and potential of β-adrenoceptor agonists and antagonists", *Eur. J. Clin. Pharmacol.* 1998, 53, 389-404.) $\beta_2$ Adrenergic receptor activity is also known to be associated with pre-term labor (see U.S. Pat. No. 5,872,126) and some types of inflammation (see WO 99/30703 and U.S. Pat. No. 5,290,815).

The term "pharmaceutically acceptable salt" means a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically acceptable acids include, but are not limited to, acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), 1,5-napthalene disulfonic and the like. Salts derived from fumaric, hydrobromic, hydrochloric, acetic, sulfuric, methanesulfonic, 1,5-napthalene disulfonic, xinafoic, oxalic, and tartaric acids are of particular interest.

Salts derived from pharmaceutically acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of Formula I.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. Other suitable amino-protecting groups are well known to one skilled in the art. See, for example, *Protective Groups in Organic Synthesis*, 3$^{rd}$ edition, T. W. Greene and P. G. M. Wuts, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like. Other suitable hydroxy-protecting groups are also well known to one skilled in the art. See, for example, *Protective Groups in Organic Synthesis*, 3$^{rd}$ edition, T. W. Greene and P. G. M. Wuts, John Wiley & Sons, New York, 1999, and Harrison and Harrison et al., *Compendium of Synthetic Organic Methods*, Vols. 1-8 (John Wiley and Sons, 1971-1996), which have been previously incorporated herein by reference.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above", "those defined herein", and "as defined herein," when referring to a variable, are used interchangeably and includes the broad definition of the variable as well as narrow definitions, if any.

Compounds of the Present Invention

The present invention provides novel compounds of Formula I. Throughout this disclosure, it is to be understood that the scope of this invention also encompasses pharmaceutically acceptable salts, solvates, and stereoisomers of compounds of Formula I. In addition, various mixtures of compounds of Formula I isomers are also within the scope of the present invention. The following exemplary and preferred values for radicals, substituents, and ranges, are for illustration only; they do not exclude other defined values or other values within defined ranges for the radicals and substituents.

In a specific aspect of the invention, $R^1$ is halo, —CH$_2$OH, or —NHCHO.

In other specific aspects, $R^1$ is chloro, —CH$_2$OH, or —NHCHO; or $R^1$ is —CH$_2$OH or —NHCHO.

In a specific aspect, $R^2$ is hydrogen.

In another specific aspect, $R^1$ and $R^2$ taken together is of the formula —NHC(=O)CH=CH— or —CH=CHC(=O)NH—.

In a specific aspect, $R^3$ is hydroxy or amino.

In other specific aspects, $R^4$ is hydrogen or halo; or $R^4$ is hydrogen or chloro.

In a specific aspect, $R^1$ is —NHCHO, $R^3$ is hydroxy, and $R^2$ and $R^4$ are each hydrogen.

In another specific aspect, $R^1$ and $R^2$ taken together are —NHC(=O)CH=CH— or —CH=CHC(=O)NH—, $R^3$ is hydroxy, and $R^4$ is hydrogen.

In yet another specific aspect, $R^1$ is —CH$_2$OH, $R^3$ is hydroxy, and $R^2$ and $R^4$ are each hydrogen.

In a specific aspect, $R^6$ is hydrogen.
In a specific aspect, $R^7$ is hydrogen.
In a specific aspect, $R^8$ is hydrogen.
In a specific aspect, $R^9$ is hydrogen.
In a specific aspect, $R^z$ is hydrogen.
In a specific aspect, $R^a$ is hydrogen or C$_{1-6}$ alkyl.
In another specific aspect, $R^a$ is hydrogen.
In a specific aspect, each of $R^b$ and $R^c$ is independently hydrogen or C$_{1-6}$ alkyl.
In another specific aspect, each of $R^b$ and $R^c$ is independently hydrogen or methyl.
In yet another specific aspect, $R^b$ and $R^c$ together with the nitrogen atom to which they are attached form a heterocyclyl ring having from 5 to 7 ring atoms and containing 1 to 3 heteroatoms selected from nitrogen, oxygen and sulfur.
In still another specific aspect, $R^b$ and $R^c$ together with the nitrogen atom to which they are attached form morpholino.

In one aspect, the invention provides compounds of Formula IA:

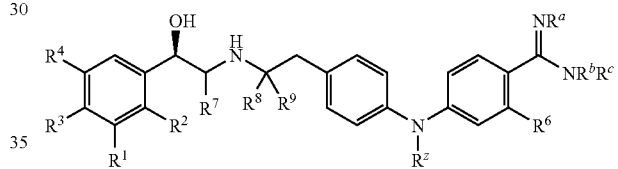

IA wherein $R^1$, $R^2$, $R^3$, $R^4$, $R^6$, $R^7$, $R^8$, $R^9$, $R^a$, $R^b$, $R^c$, and $R^z$ take any of the values defined herein.

As explicitly illustrated by compounds of Formula IA above, compounds of the present invention contain a chiral center at the alkylene carbon to which the hydroxy group is attached. When a mixture of stereoisomers is employed, it is advantageous for the amount of the stereoisomer with the (R) orientation at the chiral center bearing the hydroxy group to be greater than the amount of the corresponding (S) stereoisomer. When comparing stereoisomers of the same compound, the (R) stereoisomer is preferred over the (S) stereoisomer.

In another aspect the invention provides compounds of Formula IB:

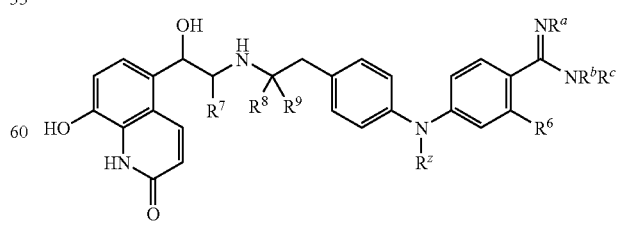

IB wherein $R^6$, $R^7$, $R^8$, $R^9$, $R^a$, $R^b$, $R^c$, and $R^z$ are as defined herein.

In yet another aspect, the invention provides compounds of Formula IC:

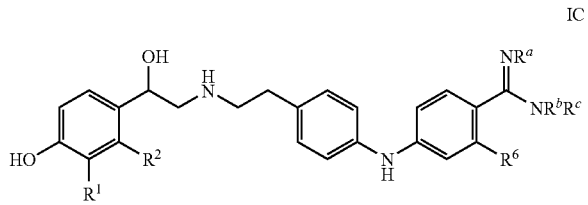

wherein $R^1$, $R^2$, $R^a$, $R^b$, $R^c$, and $R^6$ are as defined herein.

The invention further provides compounds of Formula ID:

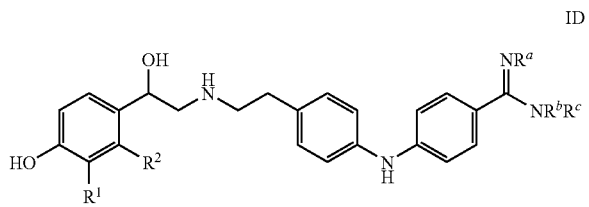

wherein
$R^1$ is —CH$_2$OH or —NHCHO and $R^2$ is hydrogen, or $R^1$ and $R^2$ taken together are —NHC(=O)CH=CH— or —CH=CHC(=O)NH—,
$R^a$ is hydrogen or C$_{1-6}$ alkyl; and
each of $R^b$ and $R^c$ is independently hydrogen, or C$_{1-6}$ alkyl, or $R^b$ and $R^c$ together with the nitrogen atom to which they are attached form a heterocyclyl ring having from 5 to 7 ring atoms and containing 1 to 3 heteroatoms selected from nitrogen, oxygen and sulfur.

In addition, the invention provides compounds of Formula ID wherein each of $R^b$ and $R^c$ is independently hydrogen or methyl.

Further the invention provides compounds of Formula ID wherein $R^b$ and $R^c$ together with the nitrogen atom to which they are attached form morpholino.

Particular mention may be made of the following compounds of the invention:
4-(4-{2-[(R)-2-hydroxy-2-(8-hydroxy-2-oxo-1,2-dihydroquinolin-5-yl)ethylamino]-ethyl}phenylamino)benzamidine;
4-(4-{2-[(R)-2-hydroxy-2-(8-hydroxy-2-oxo-1,2-dihydroquinolin-5-yl)ethylamino]-ethyl}-phenylamino)-N,N-dimethylbenzamidine; and
8-hydroxy-5-[(R)-1-hydroxy-2-(2-{4-[4-(imino-morpholin-4-yl-methyl)phenylamino]-phenyl}ethylamino)ethyl]-1H-quinolin-2-one;

where the chemical nomenclature conforms to that of the program AutoNom, provided by MDL Information Systems, GmbH (Frankfurt, Germany).

General Synthetic Procedures

Compounds of the present invention can be prepared from readily available starting materials using the following general methods and procedures. Various substituents on the compounds of the present invention can be present in the starting compounds, added to any one of the intermediates or added after formation of the final products by known methods of substitution or conversion reactions. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, 3$^{rd}$ ed., John Wiley & Sons, New York, 1999, and references cited therein, all of which are incorporated herein by reference in their entirety.

Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. While reaction times for some of the reactions are given below, one can readily monitor the progress of reaction using a variety of techniques known to one skilled in the art, such as thin layer chromatography, gas chromatography, and other chromatography methods.

In one method of synthesis, compounds of Formula I are prepared as illustrated in Scheme A. (The substituents and variables shown in the following schemes have the definitions provided above unless otherwise indicated.)

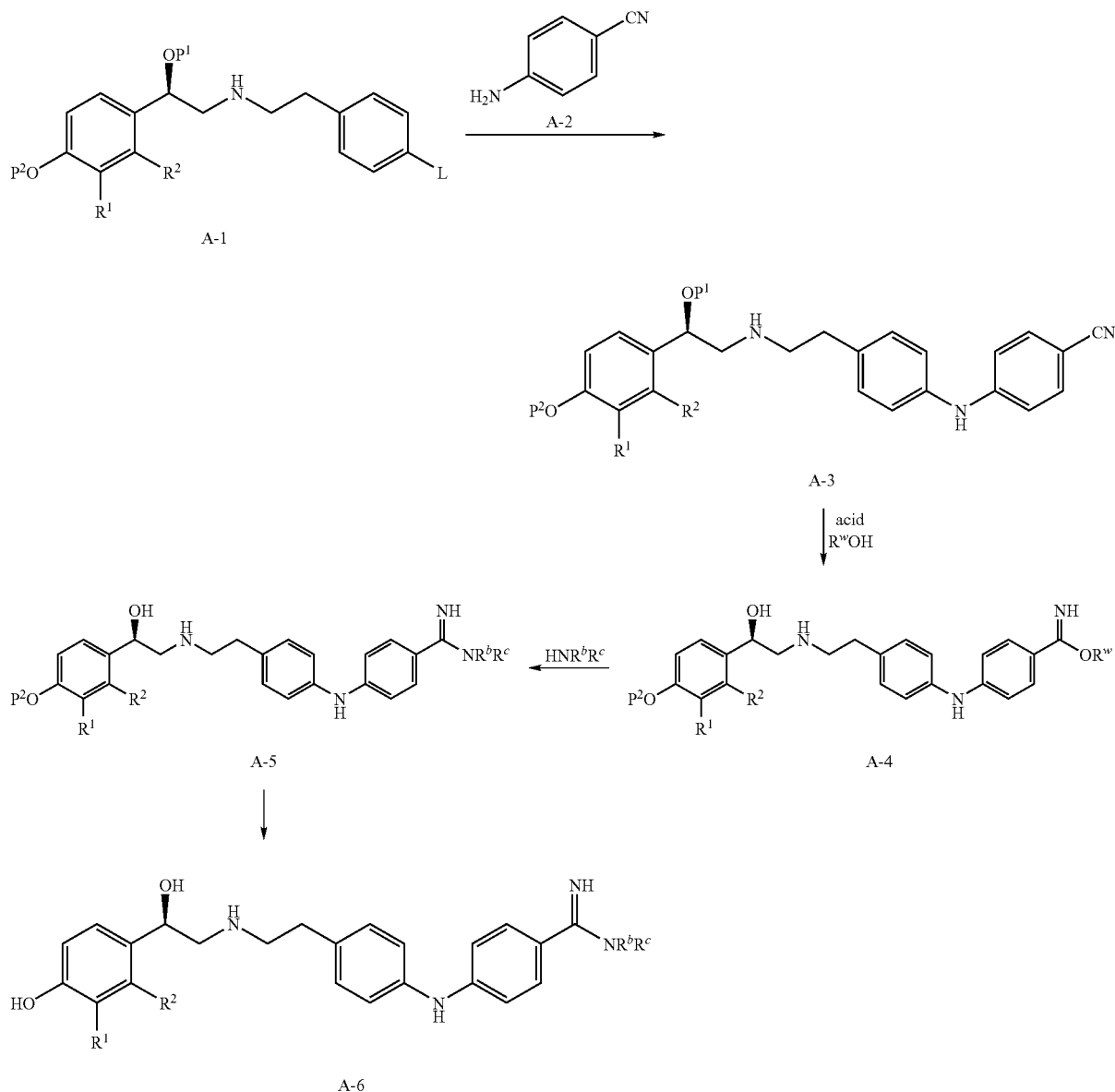

Scheme A where each of $P^1$ and $P^2$ is independently a hydroxy-protecting group, L is a leaving group, such as halo (e.g., bromo), and $R^wOH$ is an alcohol. Typically, hydroxy-protecting groups $P^1$ and $P^2$ have different reactivity, thereby allowing selective removal of one of the hydroxy-protecting groups under appropriate conditions.

As shown in Scheme A, a compound of formula A-1 is reacted with an aryl amine (A-2) to provide a coupled intermediate product of formula A-3. Typically, this coupling reaction is conducted in an organic solvent in the presence of base and a transition metal catalyst and arylphosphine ligand with heating. Useful transition metal catalysts for coupling of an aryl group to an aryl amine include palladium based catalysts, such as tris(dibenzylidenacetone)-dipalladium(0). Suitable arylphosphine ligands include rac-2,2'-bis(diphenylphosphino)-1,1'-binapthyl. The coupling reaction is typically carried out by heating the reaction mixture at a temperature of between about 50° C. and about 120° C. Often, the reaction time ranges between about 0.25 h and about 12 h.

The protecting group $P^1$ is typically an acid labile hydroxy-protecting group such as a silyl protecting group, including trialkylsilyl (e.g., tert-butyldimethylsilyl). In this manner, $P^1$ can be removed under the same reaction condition as acid hydrolysis of the cyano group to provide an imidate compound of formula A-4. A wide variety of acids can be used to hydrolyze the cyano group to an imidate group. Exemplary acids that can hydrolyze the cyano group include sulfuric acid, hydrochloric acid, hydrobromic acid, hydriodic acid, etc. Typically, this hydrolysis reaction is carried out in an alcoholic solvent, such as methanol, ethanol, or isopropanol. The reaction temperature generally ranges from 0° C. to about 50° C., often about 15° C. to about 30° C. Generally, the reaction time ranges from about 1 h to about 24 h, with about 6 h to about 12 h being a typical reaction time.

Reacting the imidate compound of formula A-4 with an amine compound of the formula $HNR^bR^c$ then provides an amidine compound of formula A-5. While the imidate compound of formula A-4 can be purified prior to reacting it with the amine compound, generally it is more convenient to use a crude, i.e., unpurified, imidate compound of formula A-4. Reaction conditions for preparing the amidine compound of formula A-5 from the imidate compound of formula A-4 depends on the reactivity of the amine compound. Typically, however, the reaction is carried out in an alcoholic solvent such as methanol or ethanol. The reaction temperature can be anywhere from 0° C. and up to the boiling point of the reaction solvent depending on the reactivity of the amine compound. Often the reaction temperature ranges from about 10° C. to about 70° C.

Removal of the protecting group $P^2$ from the amidine compound of formula A-5 then provides the product of formula A-6. Generally, the hydroxy protecting group $P^2$ is a benzyl protecting group, which is typically removed from the amidine compound of formula A-5 by hydrogenation using a palladium on carbon catalyst, to provide the product.

Alternatively, the leaving group L of the compound of formula A-1 and the amino group of the compound of formula A-2 can be interchanged such that an amino group takes the place of the leaving group L in formula A-1 and the leaving group L takes the place of the amino group in formula A-2.

Another alternative is to convert the cyano group to an amidine group (e.g., via hydrolysis and reaction with an amine compound) prior to the coupling reaction between compounds of formulas A-1 and A-2.

Intermediates of formula A-1 may be prepared by procedures known in the art, and described, for example, in U.S. Pat. Nos. 6,653,323 B2 and 6,670,376 B1, which are incorporated herein by reference, and in references therein.

Another method for preparing compounds of the present invention is illustrated in Scheme B. (The substituents and variables shown in the following schemes have the definitions provided above unless otherwise indicated.)

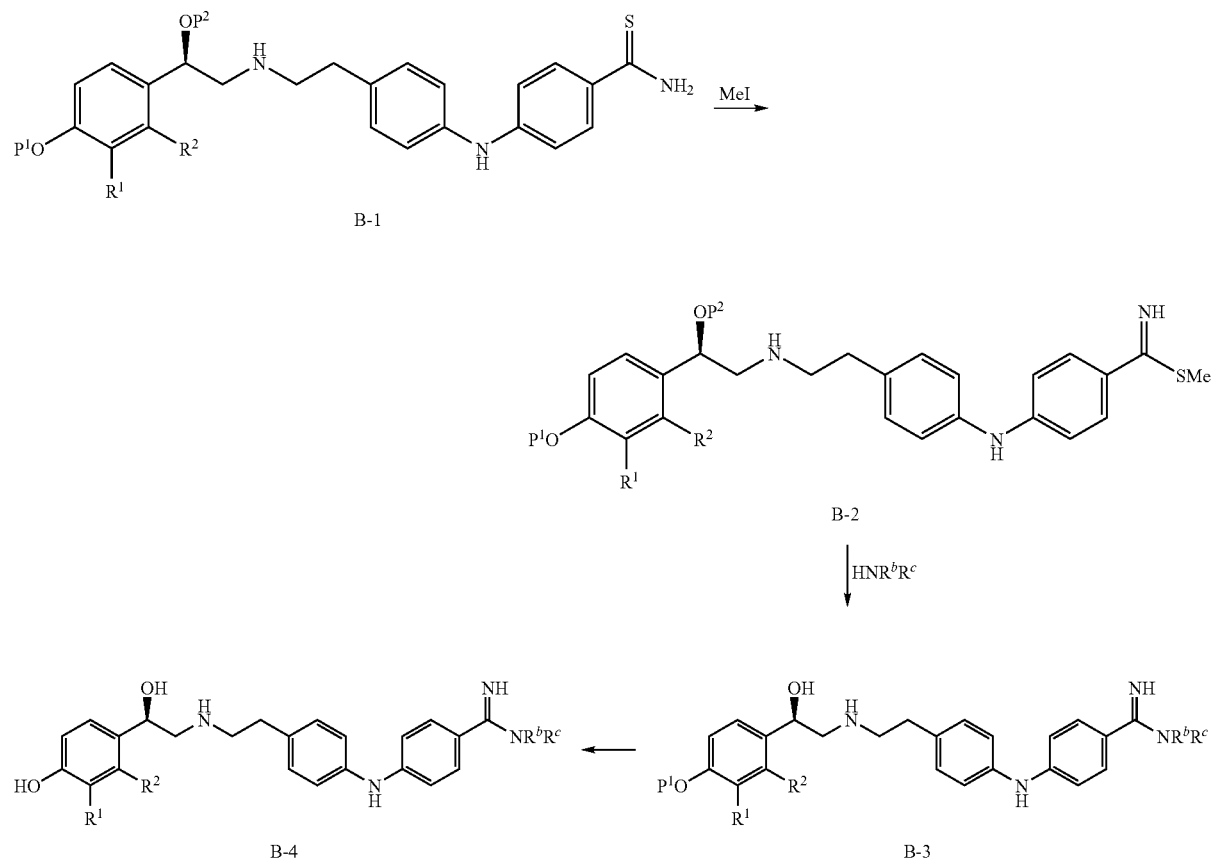

In the method illustrated in Scheme B, a thiocarbonyl compound of B-1 is methylated to yield an thioimidate B-2. Reacting the thioimidate group with an amine compound of the formula HNR$^b$R$^c$ and deprotecting the resulting intermediate affords a compound of formula B-3. Removal of the hydroxy-protecting group P$^1$ on the aromatic ring as discussed above in Scheme A then provides the compound of Formula B-4. The method can optionally use a thiocarbonyl compound in which one or both of the nitrogens of the secondary amines bears an amino-protecting group and include an additional deprotection step to remove the amino-protecting group or groups.

Intermediates of formula B-1 may be prepared, for example, by hydrolysis of the corresponding nitrile of Formula IV to the carboxamide, followed by conversion of the carboxamide to the thioamide B-1 using Lawesson's reagent.

Another method for preparing compounds of the present invention, where R$^1$ is —NHCHO and R$^2$ is hydrogen, is illustrated in Scheme C below, In Scheme C, compound C-1 is derived from a coupling reaction of the two aromatic ring compounds as described in Scheme A above. The amino groups are protected using amino-protecting groups that are stable to acidic conditions to provide a compound of formula C-2. Such protecting groups are well known to one skilled in the art and are disclosed in the above incorporated *Protecting Groups in Organic Synthesis* by Greene and Wutz. The cyano group of compound of formula C-2 is then hydrolyzed under acidic conditions (see discussion in Scheme A above) to provide an imidate compound C-3. As shown in Scheme C, acidic hydrolysis of the cyano group also removes the formyl group. Reaction of the imidate compound C-3 with an amine compound then provides the amidine compound of formula C-4. Reformylation of the free amino group of compound of formula C-4 provide a compound of formula C-5. Selective removal of the protecting group P on the nitrogen atom that is located between two Scheme C

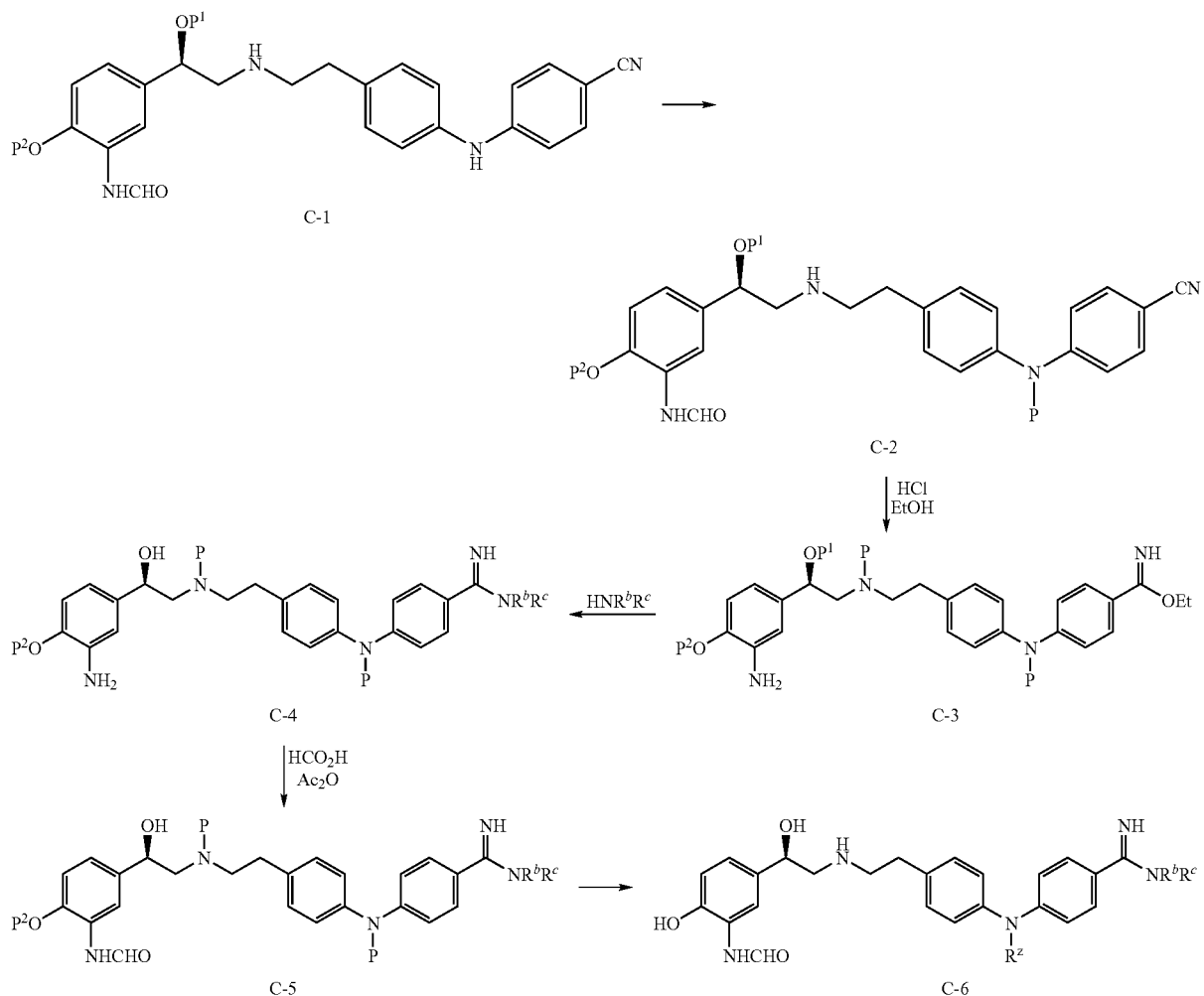

where P$^1$ and P$^2$ are independently a hydroxy-protecting group, each P is independently an amino-protecting group, and exemplary reagents and conditions are indicated explicitly.

phenyl groups in the compound of formula C-5 and subsequent functionalization of the free amino group then provides a desired substituent R$^z$ on the nitrogen atom (where R$^z$ is C$_{1-6}$ alkyl). Removal of the other amino-protecting group P then provides a compound of formula C-6. For compounds where $R^z$ is hydrogen, both amino-protecting groups P can be removed in a single reaction.

Other methods for producing an amidine functional group from other functional groups, such as cyano and imidate groups, are well known to one skilled in the art. See for example, *Advanced Organic Chemistry*, 5$^{th}$ Ed., Smith and March, 2001, John Wiley & Sons, New York, N.Y., which is incorporated herein by reference in its entirety. In this manner, a wide variety of starting materials can be used for the synthesis of compounds of Formula I.

Pharmaceutical Compositions

The invention also provides pharmaceutical compositions comprising a compound of the invention. Accordingly, the compound, typically in the form of a pharmaceutically-acceptable salt, can be formulated for any suitable form of administration, such as oral or parenteral administration, or administration by inhalation.

By way of illustration, the compound can be admixed with conventional pharmaceutical excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical excipient(s) routinely used for preparing solid compositions. Examples of such excipients include magnesium stearate, starch, lactose, sucrose, microcrystalline cellulose and binders, for example polyvinylpyrrolidone. The tablet can also be provided with a color film coating, or color included as part of the excipient(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 μm.

A typical formulation for use in a conventional nebulizer device is an isotonic aqueous solution of a pharmaceutical salt of the active agent at a concentration of the active agent of between about 0.05 μg/mL and about 1 mg/mL. Suitable nebulizer devices are provided commercially, for example, by PARI GmbH (Stamberg, Germany). Other nebulizer devices have been disclosed, for example, in U.S. Pat. No. 6,123,068.

DPI's typically administer a therapeutic agent in the form of a free flowing powder that can be dispersed in a patient's air-stream during inspiration. Alternative DPI devices which use an external energy source to disperse the powder are also being developed. In order to achieve a free flowing powder, the therapeutic agent can be formulated with a suitable excipient (e.g., lactose or starch). A dry powder formulation can be made, for example, by combining dry lactose particles with micronized particles of a suitable form, typically a pharmaceutically-acceptable salt, of a compound of the invention (i.e. the active agent) and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.001% to about 2% by weight of a compound of the invention, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing a pharmaceutical salt of the present active agent, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

The active compounds are useful as a $\beta_2$ adrenergic receptor agonist and therefore are useful for treating medical diseases or conditions mediated by $\beta_2$ adrenergic receptors or associated with $\beta_2$ adrenergic receptor activity in a mammal, i.e. medical conditions which are ameliorated by treatment with a $\beta_2$ adrenergic receptor agonist. Such medical conditions include but are not limited to a pulmonary disease, such as asthma or chronic obstructive pulmonary disease, pre-term labor, a neurological disorder, a cardiac disorder, or inflammation.

The active compounds are effective over a wide dosage range and are generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agents for inhalation administration are in the general range of from about 0.05 µg/day to about 1000 µg/day, preferably from about 0.1 µg/day to about 500 µg/day. It will be understood that the fraction of active agent delivered to the lung characteristic of particular delivery devices is taken into account in determining suitable doses for inhalation administration.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 µg/day to about 100 mg/day, preferably 0.5 to 1000 µg/day.

Among other properties, compounds of the invention exhibit surprising and unexpected duration of action. As described in the examples below, a compound of the invention demonstrated duration of action greater than 24 hours in an animal model of bronchoprotection. Furthermore compounds of the invention are potent and selective agonists of the $\beta_2$ adrenergic receptor. In particular, compounds of the invention are selective for the $\beta_2$ adrenergic receptor as compared with the $\beta_1$ and $\beta_3$ adrenergic receptors.

The invention thus provides a method of treating a mammal having a disease or condition associated with $\beta_2$ adrenergic receptor activity, the method comprising administering to the mammal a therapeutically effective amount of a compound of the invention or of a pharmaceutical composition comprising a compound of the invention.

The present active agents can also be used as part of a combination comprising, in addition, one or more other therapeutic agents. For example, the present agents can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines.

The invention thus provides, in a further aspect, a combination comprising a compound of the invention together with one or more therapeutic agent, for example, an anti-inflammatory agent, an antichlolinergic agent, another $\beta_2$ adrenergic receptor agonist, an antiinfective agent or an antihistamine. In the combinations of the invention, the individual compounds may be provided separately, for example, in an inhalation delivery device that employs separate compartments for each therapeutic agent, or may be formulated together in a single pharmaceutical composition.

The other therapeutic agents can be used in the form of pharmaceutically-acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. Representative phosphodiesterase-4 (PDE4) inhibitors or mixed PDE3/PDE4 inhibitors include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d,l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically-acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of Formula I or a pharmaceutically-acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a compound of Formula I or a pharmaceutically-acceptable salt or solvate or stereoisomer thereof and a PDE4 inhibitor.

The invention thus provides, in a further aspect, a combination comprising a compound of Formula I or a pharmaceutically-acceptable salt or solvate or stereoisomer thereof and an anticholinergic agent.

The invention thus provides, in a further aspect, a combination comprising a compound of Formula I or a pharmaceutically-acceptable salt or solvate or stereoisomer thereof and an antihistamine.

The invention thus provides, in a further aspect, a combination comprising a compound of Formula I or a pharmaceutically-acceptable salt or solvate or stereoisomer thereof together with a PDE4 inhibitor and a corticosteroid.

The invention thus provides, in a further aspect, a combination comprising a compound of Formula I or a pharmaceutically-acceptable salt or solvate or stereoisomer thereof together with an anticholinergic agent and a corticosteroid.

As used in the above combinations, the term, "a compound of Formula I" includes exemplary groups thereof, such as compounds of Formulas IA, IB, IC, ID and IE, and any individually disclosed compound or compounds.

Accordingly, the pharmaceutical compositions of the invention can optionally comprise combinations of a compound of Formula I or a pharmaceutically-acceptable salt or solvate or stereoisomer thereof with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art. Methods of treatment of the invention, therefore, include administration of the individual compounds of such combinations either sequentially or simultaneously in separate or combined pharmaceutical formulations.

Thus, according to a further aspect, the invention provides a method of treating a mammal having a disease or condition associated with $\beta_2$ adrenergic receptor activity, the method comprising administering to the mammal a therapeutically effective amount of a combination of a compound of Formula I or a pharmaceutically-acceptable salt or solvate or stereoisomer thereof with one or more other therapeutic agents.

Since compounds of the invention are $\beta_2$ adrenergic receptor agonists, such compounds are also useful as research tools for investigating or studying biological systems or samples having $\beta_2$ adrenergic receptors, or for discovering new $\beta_2$ adrenergic receptor agonists. Moreover, since compounds of the invention exhibit selectivity for $\beta_2$ adrenergic receptors as compared with binding and functional activity at receptors of other β adrenergic subtypes, such compounds are also useful for studying the effects of selective agonism of $\beta_2$ adrenergic receptors in a biological system or sample. Any suitable biological system or sample having $\beta_2$ adrenergic receptors may be employed in such studies which may be conducted either in vitro or in vivo.

Representative biological systems or samples suitable for such studies include, but are not limited to, cells, cellular extracts, plasma membranes, tissue samples, mammals: (such as mice, rats, guinea pigs, rabbits, dogs, pigs, etc.) and the like. The effects of agonizing the $\beta_2$ adrenergic receptor are determined using conventional procedures and equipment, such as radioligand binding assays and functional assays, for example the assay for ligand-mediated changes in intracellular cyclic adenosine monophosphate (cAMP) described below, or assays of a similar nature. A $\beta_2$ adrenergic receptor-agonizing amount of a compound of the invention will typically range from about 1 nanomolar to about 1000 nanomolar. When compounds of the invention are used as research tools for discovering new $\beta_2$ adrenergic receptor agonists, the invention also includes, as separate embodiments, both the generation of comparison data (using the appropriate assays) and the analysis of the test data to identify test compounds of interest.

The following non-limiting examples illustrate representative pharmaceutical compositions of the invention. Additional suitable carriers for formulations of the active compounds of the present invention can also be found in *Remington: The Science and Practice of Pharmacy, 20th Edition*, Lippincott Williams & Wilkins, Philadelphia, Pa., 2000.

FORMULATION EXAMPLE A

This example illustrates the preparation of a representative pharmaceutical composition for oral administration of a compound of this invention:

| Ingredients | Quantity per tablet, (mg) |
|---|---|
| Active Compound | 1 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
|---|---|
| Active Compound | 1 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
|---|---|
| Active Compound | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
|---|---|
| Active Compound | 0.1 mg |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition for topical application of a compound of this invention.

| Ingredients | grams |
|---|---|
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE G

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

FORMULATION EXAMPLE H

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
|---|---|
| Pharmaceutical salt of active compound | 0.2 |
| Lactose | 25 |

The pharmaceutical salt of active compound is micronized prior to blending with lactose. The contents of the cartridges are administered using a powder inhaler.

FORMULATION EXAMPLE I

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 μg and about 100 μg of active drug ingredient per dose.

FORMULATION EXAMPLE J

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

FORMULATION EXAMPLE K

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into canisters with pressurized 1,1,1,2,3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using Tests A-B below, or can be demonstrated using other tests that are known in the art.

Abbreviations:
% Eff % efficacy
ATCC American Type Culture Collection
BSA Bovine Serum Albumin
cAMP Adenosine 3':5'-cyclic monophosphate
DMEM Dulbecco's Modified Eagle's Medium
DMSO Dimethyl sulfoxide
EDTA Ethylenediaminetetraacetic acid
Emax maximal efficacy
FBS Fetal bovine serum
Gly Glycine
HEK-293 Human embryonic kidney-293
PBS Phosphate buffered saline
rpm rotations per minute
Tris Tris(hydroxymethyl)aminomethane Membrane Preparation from Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 µg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat.# 1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM MgCl$_2$, 1 mM EDTA @ 25° C.). Protein concentration of the membrane suspension was determined by the method of Bradford (Bradford M M., *Analytical Biochemistry*, 1976, 72, 248-54). Membranes were stored frozen in aliquots at −80° C.

Test A

Radioligand Binding Assay on Human $\beta_1$ and $\beta_2$ Adrenergic Receptors

Binding assays were performed in 96-well microtiter plates in a total assay volume of 100 µL with 5 µg membrane protein for membranes containing the human $\beta_2$ adrenergic receptor, or 2.5 µg membrane protein for membranes containing the human $\beta_1$ adrenergic receptor in assay buffer (75 mM Tris/HCl pH 7.4 @ 25° C., 12.5 mM MgCl$_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM-200 nM. Displacement assays for determination of p$K_i$ values of compounds were done with [$^3$H]dihydroalprenolol at 1 nM and 10 different concentrations of compound ranging from 40 pM-10 µM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 µM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @ 4° C., 12.5 mM MgCl$_2$, 1 mM EDTA) to remove unbound radioactivity. Plates were dried, 50 µL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM alprenolol. $K_i$ values for compounds were calculated from observed IC$_{50}$ values and the $K_d$ value of the radioligand using the Cheng-Prusoff equation (Cheng Y, and Prusoff W H., *Biochemical Pharmacology*, 1973, 22, 23, 3099-108). The receptor subtype selectivity was calculated as the ratio of $K_i(\beta_1)/K_i(\beta_2)$. Compounds of the invention demonstrated greater binding at the $\beta_2$ adrenergic receptor than at the $\beta_1$ adrenergic receptor, i.e. $K_i(\beta_1)>K_i(\beta_2)$ with selectivity greater than about 30.

Test B

Whole-Cell cAMP Flashplate Assays with Cell Lines Heterologously Expressing Human $\beta_1$ Adrenoceptor, $\beta_2$ Adrenoceptor, and $\beta_3$ A HEK-293 cell line stably expressing cloned human $\beta_1$ adrenergic receptor (clone H34.1) was grown to about 70%-90% confluency in medium consisting of DMEM supplemented with 10% FBS and 500 µg/mL Geneticin. A HEK-293 cell line stably expressing cloned human $\beta_2$-adrenoceptor (clone H24.14) was grown in the same medium to full confluency. A CHO-K1 cell line stably expressing cloned human $\beta_3$-adrenoceptor was grown to about 70%-90% confluency in Ham's F-12 medium supplemented with 10% FBS and with 800 µg/mL Geneticin added to every fifth passage. The day before the assay, cultures were switched to the same growth-media without antibiotics.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. For cells expressing the $\beta_1$-adrenoceptor, 10 nM ICI 118,551 were added to the stimulation buffer, and cells were incubated for 10 min at 37° C. Cells were used at final concentrations of 30,000, 40,000 and 70,000 cells/well for the $\beta_1$-adrenoceptor-, the $\beta_2$-adrenoceptor- and the $\beta_3$-adrenoceptor expressing cells, respectively. Compounds were dissolved to a concentration of 10 mM in DMSO, then diluted to 1 mM in 50 mM Gly-HCl pH 3.0, and from there serially diluted into assay buffer (75 mM Tris/HCl pH 7.4 @ 25° C., 12.5 mM MgCl$_2$, 1 mM EDTA, 0.2% BSA). Compounds were tested in the assay at 11 different concentrations, ranging from 10 µM to 9.5 pM. Reactions were incubated for 10 min at 37° C. and stopped by addition of 100 µl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 3-parameter model for sigmoidal dose-response (Hill slope=1). Agonist potencies were expressed as pEC$_{50}$ values.

Compounds of the invention demonstrated potent activity at the $\beta_2$ adrenergic receptor in this assay, as evidenced by pEC$_{50}$ values greater than about 9. In addition, the compounds tested demonstrated selectivity in functional activity at the $\beta_2$ receptor as compared with functional activity at the $\beta_1$ and $\beta_3$ receptors. In particular, compounds of the invention demonstrated EC$_{50}$($\beta_1$)/EC$_{50}$($\beta_2$) ratios of greater than about 50 and EC$_{50}$($\beta_3$)/EC$_{50}$($\beta_2$) ratios of greater than about 400.

Test C

Whole-Cell cAMP Flashplate Assay with a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat # 181-500, Biosource International, Camarillo, Calif.). The day before the assay, medium was switched to LHC-8 (No epinephrine or retinoic acid, cat # 141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM MgCl$_2$, 1 mM EDTA, 0.2% BSA).

Compounds were tested in the assay at 10 different concentrations, ranging from 10 µM to 40 pM. Maximal response was determined in the presence of 10 µM Isoproterenol. Reactions were incubated for 10 min at 37° C. and stopped by addition of 100 µl ice-cold detection buffer. Plates were sealed, incubated over night at 4° C. and counted the next morning in a topcount scintillation counter (Packard Bio-Science Co., Meriden, Conn.). The amount of cAMP produced per mL of reaction was calculated based on the counts observed for samples and cAMP standards, as described in the manufacturer's user manual. Data were analyzed by non-linear regression analysis with the GraphPad Prism Software package (GraphPad Software, Inc., San Diego, Calif.) using the 4-parameter model for sigmoidal dose-response with variable slope. Compounds of the invention tested in this assay demonstrated pEC$_{50}$ values greater than about 8.

Compound efficacy (% Eff) was calculated from the ratio of the observed Emax (TOP of the fitted curve) and the maximal response obtained for 10 µM isoproterenol and was expressed as % Eff relative to isoproterenol. The compounds tested demonstrated a % Eff greater than about 50.

Test D

Assay of Bronchoprotection Against Acetylcholine-Induced Bronchospasm in a Guinea Pig Model Groups of 6 male guinea pigs (Duncan-Hartley (HsdPoc: DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Following a 60 minute acclimation period and a 10 minute exposure to nebulized water for injection (WFI), guinea pigs were exposed to an aerosol of test compound or vehicle (WFI). These aerosols were generated from aqueous solutions using an LC Star Nebulizer Set (Model 22F51, PARI Respiratory Equipment, Inc. Midlothian, Va.) driven by a mixture of gases (CO$_2$=5%, O$_2$=21% and N$_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre- and post-nebulization weights of the filled nebulizer.

The bronchoprotective effects of compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-5 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of a 0.1 mg/mL solution of acetylcholine (Ach), (Sigma-Aldrich, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic cocktail. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways had not collapsed and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer progam enabled the collection and derivation of pulmonary values. Starting this program initiated the experimental protocol and data collection. The changes in volume over time that occured within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach was infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second) (Giles et al., 1971). Once the pulmonary function measurements were completed at minute 35 of this protocol, the guinea pig was removed from the plethysmograph and euthanized by $CO_2$ asphyxiation.

The quantity $PD_2$, which is defined as the amount of Ach needed to cause a doubling of the baseline pulmonary resistance, was calculated using the pulmonary resistance values derived from the flow and the pressure over a range of Ach challenges using the following equation. This was derived from the equation used to calculate $PC_{20}$ values in the clinic (Am. Thoracic Soc, 2000).

$$PD_2 = \text{antilog}\left[\log C_1 + \frac{(\log C_2 - \log C_1)(2R_0 - R_1)}{R_2 - R_1}\right]$$

where:

$C_1$=Second to last Ach concentration (concentration preceding $C_2$)

$C_2$=Final concentration of Ach (concentration resulting in a 2-fold increase in pulmonary resistance ($R_L$))

$R_0$=Baseline $R_L$ value $R_1$=$R_L$ value after $C_1$ $R_2$=$R_L$ value after $C_2$ Statistical analysis of the data was performed using a One-Way Analysis of Variance followed by post-hoc analysis using a Bonferroni/Dunn test. A P-value <0.05 was considered significant.

Dose-response curves were fitted with a four parameter logistic equation using GraphPad Prism, version 3.00 for Windows (GraphPad Software, San Diego, Calif.)

$$Y = \text{Min} + (\text{Max} - \text{Min})/(1 + 10^{((\log ED_{50} - X)*\text{Hillslope})}),$$

where X is the logarithm of dose, Y is the response ($PD_2$), and Y starts at Min and approaches asymptotically to Max with a sigmoidal shape.

Representative compounds of the invention were found to have significant bronchoprotective activity at time points beyond 24 hours post-dose.

The following synthetic examples are offered to illustrate the invention, and are not to be construed in any way as limiting the scope of the invention.

EXAMPLES

General: Unless noted otherwise, reagents, starting material and solvents were purchased from commercial suppliers, for example Sigma-Aldrich (St. Louis, Mo.), J. T. Baker (Phillipsburg, N.J.), and Honeywell Burdick and Jackson (Muskegon, Mich.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent ($CD_3OD$, $CDCl_3$, or DMSO-$d_6$), and spectra were acquired with a Varian Gemini 2000 instrument (300 MHz) under standard parameters; and mass spectrometric identification was performed by an electrospray ionization method (ESMS) with a Perkin Elmer instrument (PE SCEX API 150 EX).

Example 1

This example illustrates a method for preparing 4-(4-{2-[(R)-2-(8-benzyloxy-2-oxo-1,2-dihydro-quinolin-5-yl)-2-(tert-butyl-dimethyl-silanyloxy)ethylamino]ethyl}-phenylamino)benzonitrile.

To a solution of 4-aminobenzonitrile (0.661 g, 5.6 mmol), 8-benzyloxy-5-{(R)-2-[2-(4-bromo-phenyl)-ethylamino-1-(tert-butyl-dimethyl-silanyloxy)-ethyl}-1H-quinolin-2-one hydrochloride (3.0 g, 4.66 mmol), and sodium tert-butoxide (2.02 g, 20.97 mmol) in toluene (100 mL) at room temperature was added tris(dibenzylideneacetone)-dipalladium(0) (0.213 g, 0.233 mmol), followed by rac-2,2'-bis(diphenylphosphino)-1,1'-binapthyl (0.435 g, 0.699 mmol). The resulting mixture was heated at 90° C. for 2 hours, then was cooled. The solution was washed with water (500 mL), 1:1 saturated aqueous sodium chloride:water (500 mL), then dried over magnesium sulfate. The solvent was removed at reduced pressure to afford the title compound as a dark brown solid. The desired product was isolated as its trifluoroacetate salt by reverse-phase HPLC.

Example 2

This example illustrates a method for preparing 8-hydroxy-5-[(R)-1-hydroxy-2-(2-{4-[4-(imino-morpholin-4-yl-methyl)-phenylamino]-phenyl}-ethylamino)-ethyl]-1H-quinolin-2-one.

The nitrile trifluoroacetate salt of Example 1 was dissolved in ethanol and cooled in an ice bath. HCl was bubbled until the solution was saturated. The reaction vessel was sealed and stirred at room temperature overnight, then the solvents were removed under vacuum. The residue was taken up in ethanol and morpholine was added After the reaction was judged to be completed, the product was extracted and then dissolved in ethanol and hydrogenated under a hydrogen atmosphere with palladium on carbon as a catalyst. The desired product was isolated as its trifluoroacetate salt by reverse-phase HPLC. m/z: [M+H$^+$] calcd for $C_{30}H_{33}N_5O_4$: 528.26. found 528.3.

Example 3

This example illustrates a method for preparing 4-(4-{2-[(R)-2-hydroxy-2-(8-hydroxy-2-oxo-1,2-dihydro-quinolin-5-yl)-ethylamino]-ethyl}-phenylamino)-N,N-dimethyl-benzamidine.

The nitrile trifluoroacetate salt of Example 1 was dissolved in ethanol and cooled in an ice bath. HCl was bubbled until the solution was saturated. The reaction vessel was sealed and stirred at room temperature overnight, then the solvents were removed under vacuum. 2 M dimethylamine in methanol was added to the residue and it was heated to 65° C. After the reaction was judged to be completed, the product was extracted and then dissolved in ethanol and hydrogenated under a hydrogen atmosphere with palladium on carbon as a catalyst. The desired product was isolated as its trifluoroacetate salt by reverse-phase HPLC. m/z: [M+H$^+$] calcd for $C_{28}H_{31}N_5O_3$ 486.25; found 486.5.

Example 4

This example illustrates a method for preparing 4-(4-{2-[(R)-2-hydroxy-2-(8-hydroxy-2-oxo-1,2-dihydro-quinolin-5-yl)-ethylamino]-ethyl}-phenylamino)-benzanidine.

The nitrile trifluoroacetate salt of Example 1 was dissolved in ethanol and cooled in an ice bath. HCl was bubbled until the solution was saturated. The reaction vessel was sealed and stirred at room temperature overnight, then the solvents were removed under vacuum. The residue was taken up in ethanol and ammonium acetate was added, and the resulting mixture was heated. After the reaction was judged to be completed, the product was extracted and then dissolved in ethanol and hydrogenated under a hydrogen atmosphere with palladium on carbon as a catalyst. The desired product was isolated as its trifluoroacetate salt by reverse-phase HPLC. m/z: [M+H$^+$] calcd for $C_{26}H_{27}N_5O_3$ 458.22. found 458.5.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the formula:

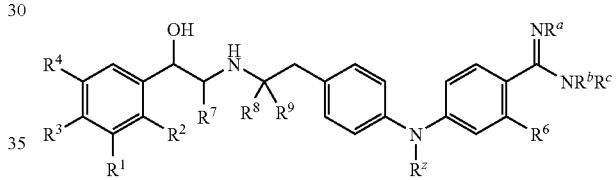

or a pharmaceutically acceptable salt or stereoisomer thereof; wherein $R^1$, $R^2$ taken together are selected from —NHC(=O)CH=CH—, and —CH=CHC(=O)NH—, $R^3$ is hydroxy and $R^4$ is hydrogen;

$R^a$ is hydrogen, $C_{1-6}$ alkyl, or hydroxy;

each of $R^b$ and $R^c$ is independently hydrogen, $C_{1-6}$ alkyl, or $C_{3-10}$ cycloalkyl, or $R^b$ and $R^c$ together with the nitrogen atom to which they are attached form a morpholinyl ring;

$R^6$ is hydrogen, hydroxy, halo, $C_{1-4}$ alkoxy, $C_{1-4}$ alkyl, or $C_{1-4}$ haloalkyl; and each of $R^7$, $R^8$, $R^9$, and $R^z$ is independently hydrogen or $C_{1-6}$ alkyl.

2. The compound according to claim 1 of the formula:

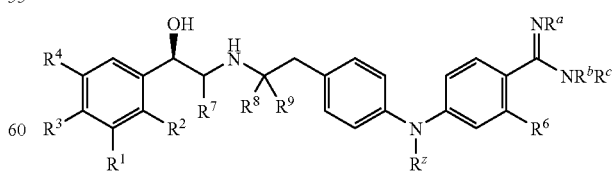

or a pharmaceutically acceptable salt thereof; wherein $R^1$, $R^2$, $R^3$, $R^4$, $R^6$, $R^7$, $R^8$, $R^9$, $R^a$, $R^b$, $R^c$, and $R^z$ are defined as in claim 1.

3. The compound according to claim 1 of the formula:

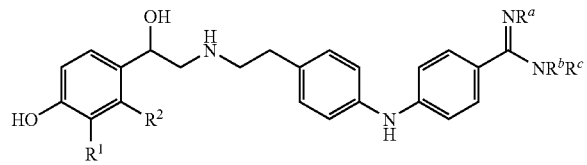

or a pharmaceutically acceptable salt or stereoisomer thereof;
wherein
  $R^1$ and $R^2$ taken together are —NHC(=O)CH=CH— or —CH=CHC(=O)NH—;
  $R^a$ is hydrogen or $C_{1-6}$ alkyl; and
  each of $R^b$ and $R^c$ is independently hydrogen, or $C_{1-6}$ alkyl, or $R^b$ and $R^c$ together with the nitrogen atom to which they are attached form a morpholinyl ring.

4. The compound according to claim 3, wherein each of $R^b$ and $R^c$ is independently hydrogen or methyl.

5. The compound according to claim 3, wherein $R^b$ and $R^c$ together with the nitrogen atom to which they are attached form morpholino.

6. The compound according to claim 3, wherein said compound is:
  4-(4-{2-[(R)-2-hydroxy-2-(8-hydroxy-2-oxo-1,2-dihydroquinolin-5-yl)ethylamino]-ethyl}phenylamino)benzamidine;
  4-(4-{2-[(R)-2-hydroxy-2-(8-hydroxy-2-oxo-1,2-dihydroquinolin-5-yl)ethylamino]-ethyl}-phenylamino)-N,N-dimethylbenzamidine;
  8-hydroxy-5-[(R)-1-hydroxy-2-(2-{4-[4-(imino-morpholin-4-yl-methyl)phenylamino]-phenyl}ethylamino)ethyl]-1H-quinolin-2-one; or
  a pharmaceutically acceptable salt thereof.

7. A pharmaceutical composition comprising a therapeutically effective amount of a compound of claim 1 or claim 6 and a pharmaceutically acceptable excipient.

8. The pharmaceutical composition of claim 7, wherein said pharmaceutical composition is formulated for administration by inhalation.

9. A process for producing an amidine substituted aryl aniline compound of Formula IF:

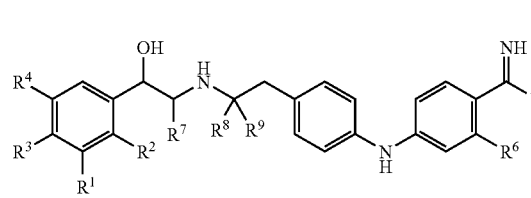

wherein $R^1$, $R^2$, $R^3$, $R^4$, $R^6$, $R^7$, $R^8$, $R^9$, $R^b$, and $R^c$ are defined as in claim 1, the process comprising:

(a) reacting an aryl compound of Formula II:

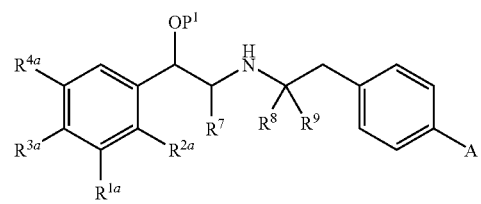

with a cyanophenyl compound of Formula III:

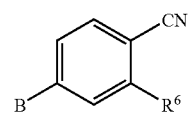

wherein
  $P^1$ is a hydroxy-protecting group,
  each of $R^{1a}$, $R^{2a}$, $R^{3a}$, and $R^{4a}$ is defined to be the same as $R^1$, $R^2$, $R^3$, and $R^4$, respectively, in claim 1, or, when any of $R^1$, $R^2$, $R^3$, and $R^4$ comprises a hydroxy or an amino group, the corresponding $R^{1a}$, $R^{2a}$, $R^{3a}$, and $R^{4a}$ group optionally comprises a protected hydroxy or a protected amino group, and
  one of A and B is halo and the other of A and B is —NH$_2$,
in the presence of a coupling catalyst under conditions sufficient to produce a cyano-substituted aryl aniline compound of Formula IV:

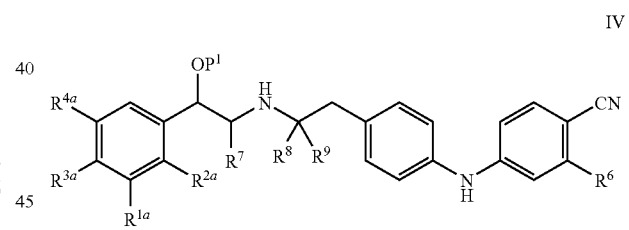

(b) reacting the cyano-substituted aryl aniline compound of Formula IV in the presence of an acid and under conditions sufficient to produce an iminoester compound of Formula VI:

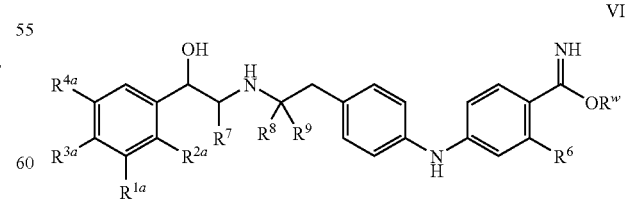

wherein $R^w$ is $C_{1-6}$ alkyl;

(c) reacting the iminoester compound of Formula VI with an amine compound of the formula HNR$^b$R$^c$ under conditions sufficient to produce a compound of Formula IG;

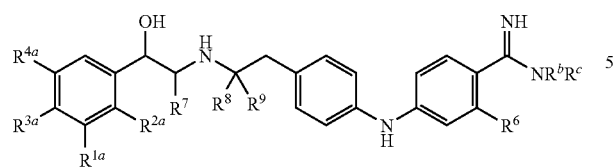
and
(d) optionally removing any hydroxy- or amino-protecting group that may be present in any of $R^{1a}$, $R^{2a}$, $R^{3a}$, and $R^{4a}$ under conditions sufficient to produce said amidine substituted aryl aniline compound of Formula IF, or a salt or stereoisomer thereof.
* * * * *